United States Patent [19]
Hammann et al.

[11] Patent Number: 4,873,347
[45] Date of Patent: Oct. 10, 1989

[54] PROCESS FOR THE PREPARATION OF THE DEMALONYL COMPOUND OF MACROLIDE LACTONES

[75] Inventors: Peter Hammann, Kelkheim; Susanne Grabley, Königstein/Taunus; Wolfgang Raether, Dreieich; Bernd Ciommer, Kelkheim; Heinz Kluge, Hofheim am Taunus; Burkhard Sachse, Kelkheim, all of Fed. Rep. of Germany

[73] Assignee: Hoechst Aktiengesellschaft, Fankfurt am Main, Fed. Rep. of Germany

[21] Appl. No.: 136,768

[22] Filed: Dec. 22, 1987

[30] Foreign Application Priority Data
Dec. 24, 1986 [DE] Fed. Rep. of Germany ....... 3644375
Jan. 8, 1987 [DE] Fed. Rep. of Germany ....... 3700331

[51] Int. Cl.$^4$ ............................................ C07D 313/00
[52] U.S. Cl. .................................... 549/267; 549/269; 549/270
[58] Field of Search ................................ 549/270, 269

[56] References Cited

U.S. PATENT DOCUMENTS 4,703,128  10/1987  Beppu et al. ...................... 549/270

FOREIGN PATENT DOCUMENTS 0178909  10/1985  European Pat. Off. .

OTHER PUBLICATIONS

Chemical Abstract, vol. 105: 168550q (Nov. 10, 1986).

*Primary Examiner*—Asok Pal
*Attorney, Agent, or Firm*—Finnegan, Henderson, Farabow, Garrett, and Dunner

[57] ABSTRACT

It is possible to prepare the demalonyl compound of macrolide lactones by hydrolysis in the presence of a base without a retro-aldol cleavage occurring.

9 Claims, No Drawings

PROCESS FOR THE PREPARATION OF THE DEMALONYL COMPOUND OF MACROLIDE LACTONES

Macrolide lactones having malonic hemiesters such as, for example, niphimycin, guanidylfungin A, copiamycin or azalomycin $F_4$ show a distinctly greater antifungal action after elimination of the hemiesters. The demalonyl compounds are fungicides, whereas the stating compounds have only fungistatic activity [K. Takesako, J. Antibiot. 28, 1363, (1985); K. Takesako, J. Antibiot. 29, 713 (1986)]. Moreover, the solubility in water of the demalonyl compounds is better.

Direct hydrolysis of the macrolide malonic hemiester to give the corresponding demalonyl compound has hitherto been regarded as impossible. Because of the hydroxyl group in the B-position to the hemiacetal group in the six-membered ring of niphimycin, for example, a retroaldol cleavage takes place on direct hydrolysis. This results in a mixture of several components, and fractionation of this has not hitherto succeeded [J. W. Westley, J. Chem. Soc. Chem. Commun. 71 (1970): K. Takesako, J. Antibiot. 28, 1363, (1985), W. Keller-Schierlein, Helv. Chim. Acta 66, 226 (1983)].

Admittedly, elimination of the malonic acid groups is possible after alkylation of the said hemiacetal group in the macrolide lactones mentioned. However, it is known that the biological action of alkylmacrolides of this type is not as good [K. Takesako, J. Antibiot. 28, 1363 (1985) and 29, 713 (1986)].

It has now been found, surprisingly, that direct hydrolytic elimination of the malonic acid groups is possible, without retro-aldol cleavage, in the presence of a base under suitable conditions.

Hence the invention relates to a process for the preparation of the demalonyl compound of macrolide lactones, which comprises hydrolysis, in the presence of a base, of the compound of the general formula I

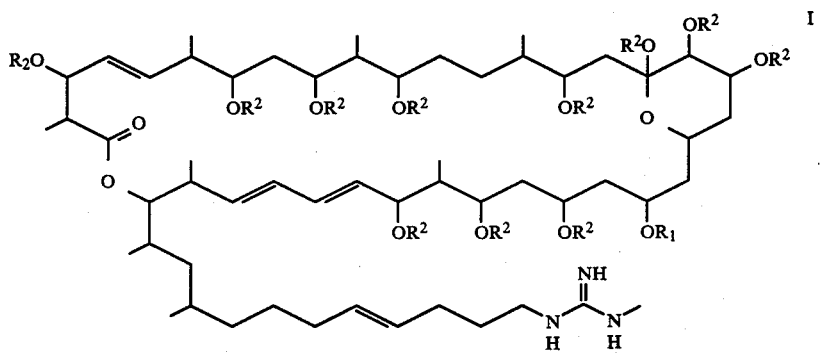

in which $R^1$ and $R^2$, independently of one another, are hydrogen or a malonyl group, not more than one $R^2$ substituent representing a malonyl group, excepting the compound of the formula I in which $R^1$ and all $R^2$ are simultaneously hydrogen.

The invention, especially the preferred embodiments, is described in detail hereinafter. The invention is also defined in the patent claims.

The compound of the general formula I is dissolved in a suitable solvent. Examples which can be used are polar solvents such as water, alcohols or mixtures thereof. Preferred solvents are lower alcohols such as, for example, methanol, ethanol, n-propanol. isopropanol and n-, iso- or tertiary butanol.

Suitable bases are added to the solutions. Amines and metal hydroxides such as, for example, alkaline earth or alkali metal hydroxides, with preference being given in turn to sodium hydroxide or potassium hydroxide from the latter group, are suitable. Good results have also been obtained on use of alcoholates as bases, in particular using alkaline earth and alkali metal alcoholates of lower alcohols, particular preference being given to sodium alcoholates and potassium alcoholates. When the compound which is to be hydrolyzed has previously been dissolved in an alcohol, it is expedient to use the alcoholate of this alcohol for the hydrolysis.

The reaction can take place at temperatures from $-30°$ C. to $+60°$ C. However, the preferred temperature range which is used is from $0°$ to $40°$ C., in particular room temperature. The length of the incubation of the mixture of compound which is to be hydrolyzed and base varies with the reaction temperature. An incubation time of about 5 to 60 hours, in particular 24 hours, has proved advantageous.

It is possible by means of the reaction time to control the number of malonyl groups which are to be eliminated. Thus, for example, under the abovementioned conditions niphimycin (1 malonyl group) can be prepared from amycin (2 malonyl groups) with a reaction time of about 1 to 3 hours.

The subsequent intended use decides whether the hydrolyzed compound is isolated. For the isolation, the pH of the reaction mixture is adjusted to a value in the range 6 to 8. After the solvent has been removed by distillation, the compound is purified by fractionation on suitable adsorbents, for example silica gel, alumina etc., and elution with polar organic solvents or mixtures thereof.

The invention is explained in detail in the examples which follow. Unless otherwise indicated, percentage data relate to weight.

EXAMPLES

1. Preparation of the demalonyl compound a. 1 g of amycin (0.81 mmol) in 75 ml of methanol is stirred with 100 mg of sodium hydride (50% suspension in oil) at 20° C. for 24 hours. Neutralization with 5N hydrochloric acid is followed by removal of the alcohol by vacuum distillation. The resulting syrup is chromatographed on 100 g of silica gel using ethyl acetate/methanol/water (15:2:1, 800 ml and 8:2:1; v:v:v). Crystallization from ethyl acetate/methanol yields 770 mg (90%) of demalonyl compound, in which $R^1$ and all $R^2$ denote hydrogen.

b. 1 g of niphimycin (0.87 mmol) in 50 ml of methanol is stirred with 60 mg of sodium hydride (50% suspension in oil) at 20° C. for 24 h. Neutralization with 5N hydrochloric acid is followed by working up as described in Example 1. 808 mg (88%) of demalonyl compound, in which $R^1$ and all $R^2$ denote hydrogen, are obtained.

c. The process is carried out as in Example 1, but the reaction is stopped after 2 hours, and 920 mg (93%) of niphimycin are obtained.

2. Use of the demalonyl compound as antimycotic agent

The in vitro tests for an antimycotic action are carried out in serial dilution tests on yeasts (Candida albicans) and molds (Aspergillus niger) [Material and Methods: Microtitration technique published in Mykosen 27, 14 (1984)]. As can be seen from Table A, in these in vitro tests the demalonyl compound, in which $R^1$ and all $R^2$ denote hydrogen, prepared according to the invention shows good antimycotic properties which are superior to those of the reference substance niphimycin.

| Product | Minimum inhibitory concentration (μg/ml) for | |
|---|---|---|
| | Candida albicans | Aspergillus niger |
| Niphimycin | 7.8 | 3.9 |
| Demalonyl compound | 3.9 | 1.95 |

We claim:

1. A process for the preparation of the demalonyl compound of macrolide lactones, which comprises hydrolysis, in the presence of a base, of the compound of the formula I

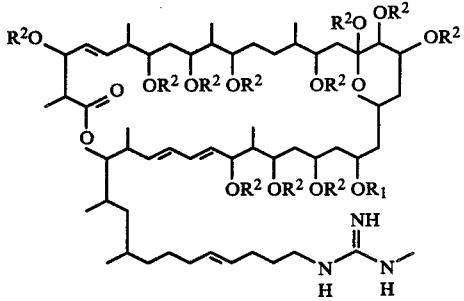

in which $R^1$ and $R^2$, independently of one another, are hydrogen or a malonyl group, not more than one $R^2$ substituent representing a malonyl group, excepting the compound of the formula I in which $R^1$ and all $R^2$ are simultaneously hydrogen.

2. The process as claimed in claim 1, wherein amines, alkali metal or alkaline earth metal hydroxides and/or alkali metal or alkaline earth metal alcoholates are used as bases.

3. The process as claimed in claim 2, wherein sodium hydroxide or potassim hydroxide and/or sodium or potassium alcoholates of lower alcohols are used as bases.

4. The process as claimed in claim 1, wherein the reaction is carried out in a lower alcohol as solvent.

5. The process as claimed in claim 1, wherein the reaction is carried out at $-30°$ C. to $+60°$ C.

6. The process as claimed in claim 5, wherein the reaction is carried out at 0° to 40° C.

7. The process as claimed in claim 6, wherein the reaction is carried out at room temperature.

8. The process as claimed in claim 1, wherein the reaction mixture is incubated for a period of 5 to 60 hours.

9. The process as claimed in claim 1 wherein the hydrolysis is direct hydrolysis of the malonic acid groups.

* * * * *